(12) United States Patent
Siri et al.

(10) Patent No.: US 9,156,800 B2
(45) Date of Patent: Oct. 13, 2015

(54) ANALOGUES OF PORPHYRINS, THEIR METHOD OF PREPARATION AND USE THEREOF

(71) Applicants: UNIVERSITÉ D'AIX-MARSEILLE, Marseilles (FR); UNIVERSITÉ DE NANTES, Nantes (FR); CENTRE NATIONAL DE LA RECHERCHE SCIENTIFIQUE (C.N.R.S), Paris (FR)

(72) Inventors: Olivier Siri, Belcodene (FR); Zhongrui Chen, Beijing (CN); Denis Jacquemin, Nantes (FR)

(73) Assignees: UNIVERSITÉ D'AIX-MARSEILLE, Marseilles (FR); UNIVERSITÉ DE NANTES, Nantes (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/424,255

(22) PCT Filed: Sep. 2, 2013

(86) PCT No.: PCT/EP2013/068111
§ 371 (c)(1),
(2) Date: Feb. 26, 2015

(87) PCT Pub. No.: WO2014/033305
PCT Pub. Date: Mar. 6, 2014

(65) Prior Publication Data
US 2015/0210653 A1   Jul. 30, 2015

(30) Foreign Application Priority Data

Aug. 31, 2012   (EP) .................................. 12306044

(51) Int. Cl.
| | | |
|---|---|---|
| C07D 257/02 | (2006.01) | |
| C07D 257/10 | (2006.01) | |
| C07F 15/00 | (2006.01) | |
| H01L 51/00 | (2006.01) | |
| H01G 9/20 | (2006.01) | |
| H01L 51/44 | (2006.01) | |

(52) U.S. Cl.
CPC .......... C07D 257/10 (2013.01); C07F 15/0093 (2013.01); H01G 9/2059 (2013.01); H01L 51/0077 (2013.01); H01L 51/0087 (2013.01); H01L 51/441 (2013.01); H01L 2251/301 (2013.01); H01L 2251/303 (2013.01)

(58) Field of Classification Search
CPC .................................................... C07D 257/02
See application file for complete search history.

(56) References Cited

U.S. PATENT DOCUMENTS

2010/0125136 A1   5/2010   Yeh et al.

FOREIGN PATENT DOCUMENTS

| CN | 101088992 A | 12/2007 |
|---|---|---|
| GB | 989560 A | 4/1965 |
| JP | 2007055946 A | 3/2007 |
| JP | 2007214364 A | 8/2007 |
| WO | 03011286 A1 | 2/2003 |
| WO | 2006038823 A1 | 4/2006 |

OTHER PUBLICATIONS

H. Winnischofer et al.: "Conduction and photoelectrochemical properties of monomeric and electropolymerized tetraruthenated porphyrin films", Photochemical & Photobiological Sciences, vol. 4, No. 4, 2005, pp. 359-366.
S. Cherian et al.: "Adsorption and Photoactivity of Tetra(4-carboxyphenyl)porphyrin (TCPP) on Nanoparticulate TiO2", Journal of Physical Chemistry B, vol. 104, No. 5, 2000, pp. 3624-3629.
M. Touil et al: "Synthesis and Properties of the Emerging Azacalix[1(4)]arenes", European Journal of Organic Chemistry, No. 10, 2011, pp. 1914-1921.
J. L. Katz et al.: "Synthesis of Inherently Chiral Azacalix[4]arenes and Diazadioxacalix[4]arenes", Organic Letters, vol. 12, No. 19, 2010, pp. 4300-4303.
Gang Qian et al: "Near-Infrared Organic Compounds and Emerging Applications", Chemistry—An Asian Journal, vol. 5, 2010, pp. 1006-1029.
A. Muranaka et al.: "[18]/[20]pi Hemiporphyrazine: A Redox-Switchable Near-Infrared Dye", Journal of the American Chemical Society, vol. 134, No. I, Jan. 11, 2012, pp. 190-193.
International Search Report and Written Opinion issued in related International Application No. PCT/EP2013/068111 on Dec. 10, 2013.

*Primary Examiner* — Sun Jae Yoo
(74) *Attorney, Agent, or Firm* — Meunier Carlin & Curfman LLC

(57) ABSTRACT

The present invention relates to compound of formula (I), their method of preparation and use thereof in particular in the fields of optoelectronic, photonic, photovoltaics and biology.

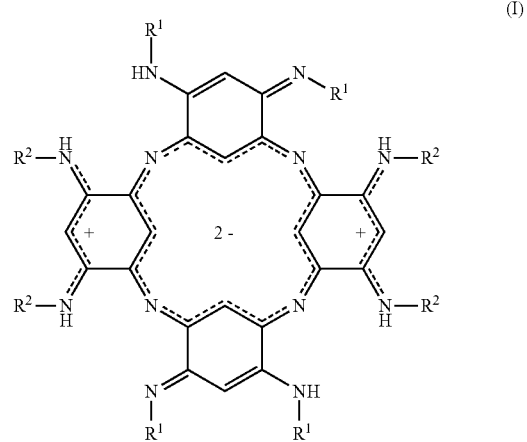

(I)

20 Claims, 3 Drawing Sheets

ANALOGUES OF PORPHYRINS, THEIR METHOD OF PREPARATION AND USE THEREOF

FIELD OF THE DISCLOSURE

The present invention concerns pyrrol-free analogues of porphyrins, their method of preparation and their use thereof especially in the fields of photonics, organic electronics including photovoltaics, optoelectronics and biology including photodynamic therapies.

BACKGROUND

π-conjugated organic molecules (cyclic and/or linear) are widely used in the field of photonics, organic electronics including photovoltaics, optoelectronics and biology due to their geometrical and electronic structures which give them unique properties. The optic and electronic properties of those π-conjugated organic molecules are linked to a parameter named HOMO-LUMO gap (Eg) which corresponds to the energy difference between the Highest Occupied Molecular Orbital (HOMO) and the Lowest Unoccupied Molecular Orbital (LUMO). This gap should be as low as possible for the above-mentioned applications.

The molecules presenting a low Eg gap are often molecules of high dimensions. However, those molecules are weakly soluble which could be a huge limitation for the above mentioned applications. It is thus important to find new π-conjugated molecules that could present a low Eg gap and which could be soluble in organic medium and water.

Photodynamic therapy (PDT) is a form of phototherapy using nontoxic light-sensitive compounds that are exposed selectively to light, whereupon they becomes toxic to targeted malignant and other diseased cells, and thus can be used in the treatment of cancer for example. Most modern PDT applications involve three key components: a photosensitizer, a light source and oxygen. The wavelength of the light source needs to be appropriate for exciting the photosensitizer to produce reactive oxygen species. The combination of these three components leads to the chemical destruction of any tissues which have either selectively taken up the photosensitizer or have been locally exposed to light. This method has some disadvantages since only cancers accessible to light can be treated such as cancers near the surface of the skin (for example red light only has a penetration of about 1 cm in living tissues). In order to treat other cancers which require a higher penetration into the tissues, the photosensitizer used should absorb in the near infrared region (NIR region) as those radiations penetrate more deeply in the skin.

Regarding photovoltaic technology, about 50% of the solar energy is in the near infrared region. Thus one of the major limiting factors for organic solar cells is the gap between the spectral absorption of the active layer and the solar emitting spectrum. The organic devices actually use various molecules in order to absorb the major part of the solar energy (from visible to near infrared). The use of a unique organic molecule absorbing on a large scale would enable an improvement in yield and costs. Organic solar cells are based on a blend or an electron donor and hole transporting material (such as polythiophene) mixed with an electron acceptor and electronic conductor material (generally fullerene derivatives). Most of the photovoltaic cells actually used are based on silicon. However, this material is expensive and difficult to recycle. Dye-photosensitized solar cells, also called Grätzel (or Graetzel) cells, have been developed based on sensitized inorganic/organic hybride semi-conductors instead of silicon. In Grätzel cell, upon photo absorption, the dye injects an electron in the conduction band of the semi-conductor. These cells especially implement less expensive material, simple and low cost production techniques. Modules obtained are semi-flexible and semi-transparent which also open larger fields of application. There is thus a need to develop dyes for this type of solar cells which can have an improved photoconversion efficiency.

Among the π-conjugated molecules, porphyrins are probably the most important and adaptable macrocycles. The major research activity on porphyrins covers a broad area ranging from chemistry, materials science, physics, biology, engineering and medicine. Porphyrins are highly conjugated heterocyclic macrocycles composed of four pyrrol subunits interconnected via one-atom bridges forming a 16-membered central ring. These porphyrins present 18 delocalized π-electrons. However, these porphyrins do not absorb in the NIR region.

Also known from Muranaka et al (JACS, 2012, 134, 190-193) are analogues of hemiporphyrazine which absorb in the NIR region. However, these compounds are not versatile since their modifications are very limited. Indeed, it should be very useful to modify the macrocyclic molecule in order to modulate the Eg gap, the control the solubility, the geometry . . . .

As a consequence there is a need to provide new macrocyclic molecules having small dimensions, low Eg gap, absorptions in the NIR region, and for which properties can be easily tailored upon chemical modifications (i.e. which are versatile).

SUMMARY

The objective of the present invention is to provide aromatic macrocycles of small dimensions, high symmetry and which are stable over time in various media.

Another objective of the present invention is to provide such macrocycles which can be easily modified (versatile).

Another objective is also to provide such macrocycles which can absorb light in a large spectral range and more specifically in the NIR region.

Another objective of the present invention is also to provide macrocycles which can be used in solar cells, such as in organic solar cells and particularly as dye for dye-sensitized solar cells (Grätzel cells).

Other objectives should appear by reading the below description of the invention.

All these objectives are met by the compounds according to the invention which comprise a central 16-membered ring bearing four nitrogen atoms and 18 π-electron and four 6-membered ring subunits.

DETAILED DESCRIPTION

The present invention relates to compound of formula (I):

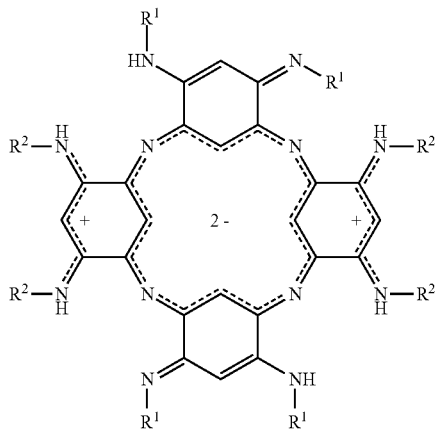

in which:

⫽ represents a single bond or a double bond provided that the central ring comprising 16 members (4 nitrogen atom and 12 carbon atoms) is an aromatic ring;

each $R^1$ and $R^2$ are identical or different and represent:
a hydrogen atom;
a group of formula $-CH(R^3)R^4$;
a group of formula $-[C(R^5)=(CR^6)]_nR^4$;
a group of formula $-C(O)R^7$; or
a group of formula $SO_2R^8$;

$R^3$ represents a hydrogen atom, an aliphatic chain, linear or branched, having from 1 to 30 carbon atoms;

$R^4$ represents an aliphatic chain, linear or branched, having from 1 to 10 carbon atoms, H, X, OH, $OR^3$, SH, $SR^3$, CH(O), C(O)OH, CX(O), $C(O)OR^3$, $C(O)NHR^3$, $C(O)NH_2$, $NHR^3$, NRR', an heteroaryl, an aryl, CN, $NO_2$, heterocycle or cycloalkyl, the heteroaryl, aryl, heterocycle or cycloalkyl is optionally substituted by one or more alkyl, linear or branched, having from 1 to 10 members, X, NRR', OR;

$R^5$ and $R^6$, identical or different, represent $R^3$, X, OH, $OR^3$, SH, $SR^3$, CH(O), C(O)OH, CX(O), $C(O)OR^3$, $C(O)NHR^3$, $C(O)NH_2$, NRR', an heteroaryl, an aryl, CN, $NO_2$, heterocycle or cycloalkyl, the heteroaryl, aryl, heterocycle or cycloalkyl is optionally substituted by one or more alkyl, linear or branched, having from 1 to 10 members, X, NRR', OR;

n is an integer from 1 to 10;

$R^7$ represents $CHR^3R^4$, heteroaryl or aryl, the heteroaryl or aryl is optionally substituted by one or more alkyl, linear or branched, having from 1 to 10 members, X, NRR', OR;

$R^8$ represents heteroaryl or aryl, the heteroaryl or aryl is optionally substituted by an alkyl, linear or branched, having from 1 to 10 members, X, NRR', OR;

X represents an halogen atom;

R, R', identical or different, represent a hydrogen atom, an aliphatic chain, linear or branched, having from 1 to 30 carbon atoms, or an aryl, the aryl is optionally substituted by one or more alkyl, linear or branched, having from 1 to 10 members, X, OH, $NH_2$; and the corresponding compound in ionic forms and in their chelated forms with metals.

Preferably:
$R^1$ and $R^2$, identical or different are H or $-C(R^3)R^4$ or alkyl, where $R^3$ is H or an aliphatic chain with 1 to 30 carbon atoms and $R^4$ is COOH or an aliphatic chain with 1 to 30 carbon atoms; or $R^3$ represents an alkyl, linear or branched, having from 1 to 18 carbon atoms; and/or $R^4$ represents a group methyl, H, X, OH, $OR^3$, SH, $SR^3$, CH(O), C(O)OH, CX(O), $C(O)OR^3$, $C(O)NHR^3$, $C(O)NH_2$, $NH_2$, $NHR^3$, NRR', an heteroaryl, an aryl, CN, $NO_2$, heterocycle or cycloalkyl, the heteroaryl, aryl, heterocycle or cycloalkyl is optionally substituted by one or more alkyl, linear or branched, having from 1 to 10 members, X, $NH_2$, OH, OR; and/or $R^5$ and $R^6$, identical or different, represent $R^3$, X, OH, $OR^3$, SH, $SR^3$, CH(O), C(O)OH, CX(O), $C(O)OR^3$, $C(O)NHR^3$, $C(O)NH_2$, NRR', an heteroaryl, an aryl, CN, $NO_2$, heterocycle or cycloalkyl, the heteroaryl, aryl, heterocycle or cycloalkyl is optionally substituted by one or more alkyl, linear or branched, having from 1 to 10 members, X, $NH_2$, OH, OR; and/or n is an integer from 1 to 10; and/or $R^7$ represents $R^3$, heteroaryl or aryl, the heteroaryl or aryl is optionally substituted by one or more alkyl, linear or branched, having from 1 to 10 members, X, $NH_2$, OH, OR; and/or $R^8$ represents heteroaryl or aryl, the heteroaryl or aryl is optionally substituted by an alkyl, linear or branched, having from 1 to 10 members, X, $NH_2$, OH, OR; and/or X represents an halogen atom; and/or R, R', identical or different, represent an aliphatic chain, linear or branched, having from 1 to 6 carbon atoms, or an aryl, the aryl is optionally substituted by one or more alkyl, linear or branched, having from 1 to 10 members, X, OH, $NH_2$.

Preferably:
$R^1$ and $R^2$ are H; and/or
$R^3$ represents an alkyl, linear or branched, having from 1 to 18 carbon atoms; and/or $R^4$ represents a group methyl, H, X, OH, $OR^3$, SH, $SR^3$, CH(O), C(O)OH, CX(O), $C(O)OR^3$, $C(O)NHR^3$, $C(O)NH_2$, $NH_2$, $NHR^3$, NRR', an heteroaryl, an aryl, CN, $NO_2$, heterocycle or cycloalkyl, the heteroaryl, aryl, heterocycle or cycloalkyl is optionally substituted by one or more alkyl, linear or branched, having from 1 to 10 members, X, $NH_2$, OH, OR; and/or $R^5$ and $R^6$, identical or different, represent $R^3$, X, OH, $OR^3$, SH, $SR^3$, CH(O), C(O)OH, CX(O), $C(O)OR^3$, $C(O)NHR^3$, $C(O)NH_2$, NRR', an heteroaryl, an aryl, CN, $NO_2$, heterocycle or cycloalkyl, the heteroaryl, aryl, heterocycle or cycloalkyl is optionally substituted by one or more alkyl, linear or branched, having from 1 to 10 members, X, $NH_2$, OH, OR; and/or n is an integer from 1 to 10; and/or $R^7$ represents $R^3$, heteroaryl or aryl, the heteroaryl or aryl is optionally substituted by one or more alkyl, linear or branched, having from 1 to 10 members, X, $NH_2$, OH, OR; and/or $R^8$ represents heteroaryl or aryl, the heteroaryl or aryl is optionally substituted by an alkyl, linear or branched, having from 1 to 10 members, X, $NH_2$, OH, OR; and/or X represents an halogen atom; and/or R, R', identical or different, represent an aliphatic chain, linear or branched, having from 1 to 6 carbon atoms, or an aryl, the aryl is optionally substituted by one or more alkyl, linear or branched, having from 1 to 10 members, X, OH, $NH_2$.

In a specific embodiment, in the compound of the invention $R^1$ and $R^2$, identical or different are H or —C($R^3$)$R^4$ or alkyl, where $R^3$ is H or an aliphatic chain with 1 to 30 carbon atoms and $R^4$ is COOH or an aliphatic chain with 1 to 30 carbon atoms.

In a specific embodiment, in the compound of the invention $R^1$ and $R^2$, identical or different are H or —C($R^3$)$R^4$ or alkyl, where $R^3$ is H or an aliphatic chain with 1 to 30 carbon atoms and $R^4$ is COOH or an aliphatic chain with 1 to 30 carbon atoms and at least one of $R^1$ or $R^2$ is different from H.

Preferably, the compound according to the invention are chosen among:

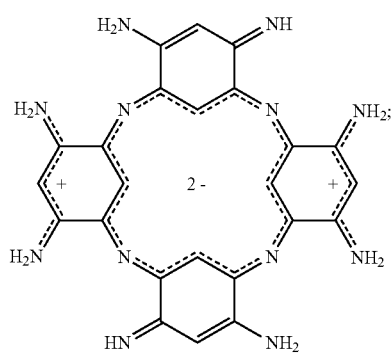

Z = Cl (I.2);

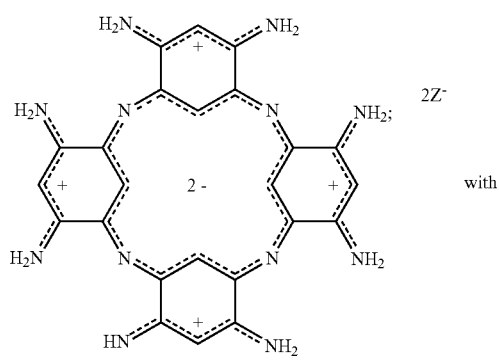

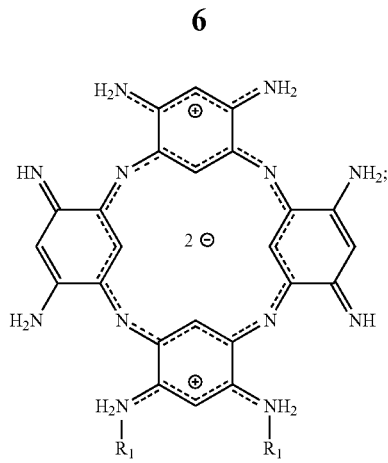

with R1 = CH₂COOH (I.3);
R1 = CH₂COOH (I.4)

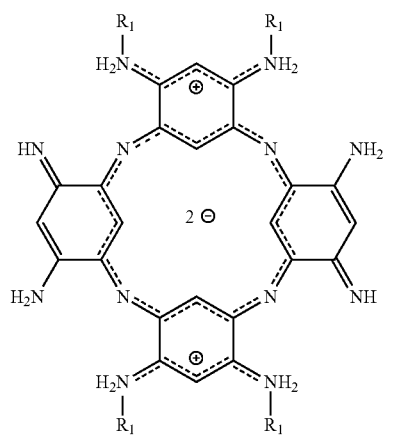
with

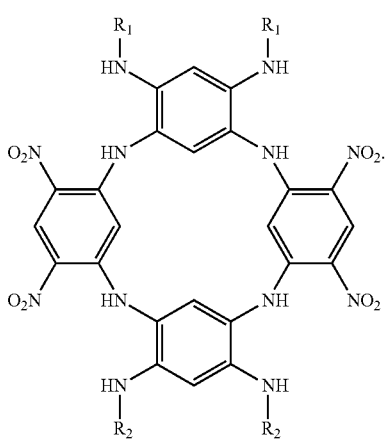
with R1 = CH₂COOH and R2 = n-butyl

It should be understood that compounds of formula (I) according to the invention are bis-zwitterionic compounds in which two positive charges and two negative charges are delocalized.

It should also be understood that ⫽ represents either a single bond or a double bond, which are delocalized in the cycle. Formula (I) comprises especially the following formulae:

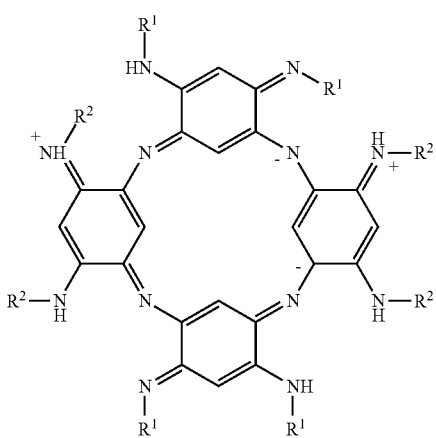

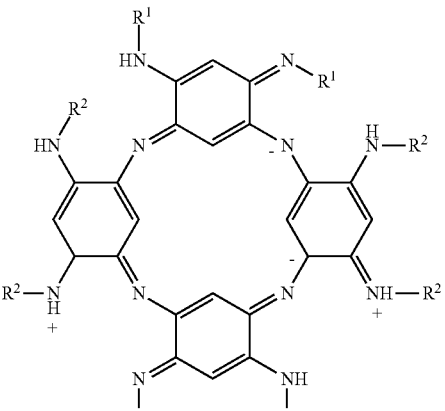

Those formulae show the delocalisation of the positive charge but it should be understood that the negative charge is also delocalisable in the central ring.

As mentioned above, the invention also relates to compounds of formula (I) in their ionic forms. Those compounds in ionic forms can be obtained by reacting the bis-zwitterionic compounds of formula (I) with at least one mole of an acid. The acid being preferably chosen among $CF_3COOH$ or HX, X having the definition given above or $BF_4^-$, $PF_6^-$, $ClO_4^-$ etc. . . . ), preferably X has the definition given above. Those compounds in ionic form can be as follows:

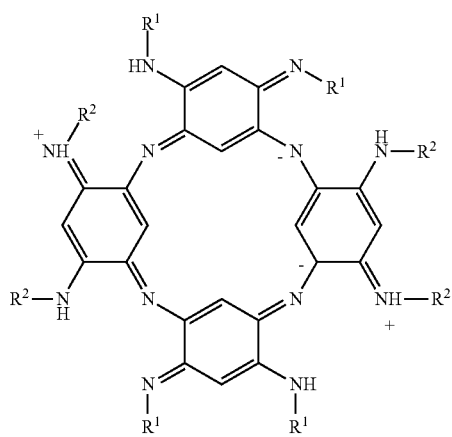

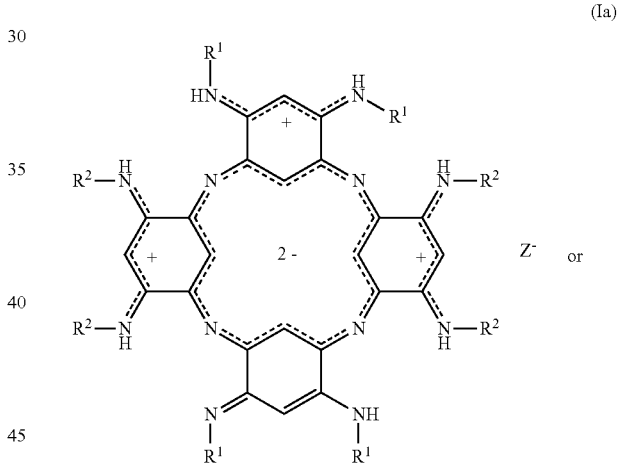

(Ia)

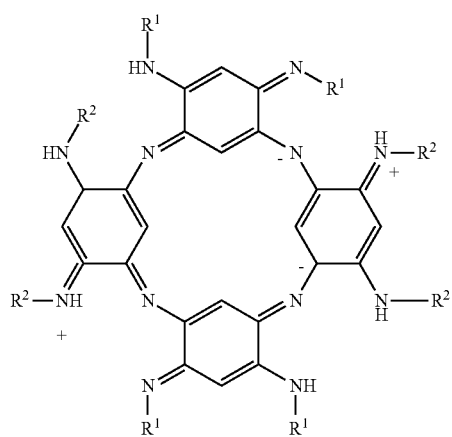

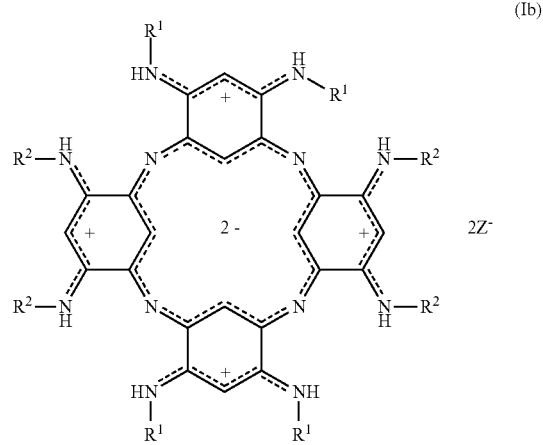

(Ib)

wherein Z represents an anion, preferably X, $BF_4$, $PF_6$, $ClO_4$, or $CF_3COO$, preferably X or $CF_3COO$.

Preferably, the compounds in ionic form are of formula (Ib).

The compounds in ionic form can also be obtained by reacting the bis-zwitterionic compounds of formula (I) with at least one mole of a base. The base is preferably chosen among strong base, for example base chosen among $NEt_3$, NaOtBu, BuLi, NaOH. Those compounds in ionic form can be as follows:

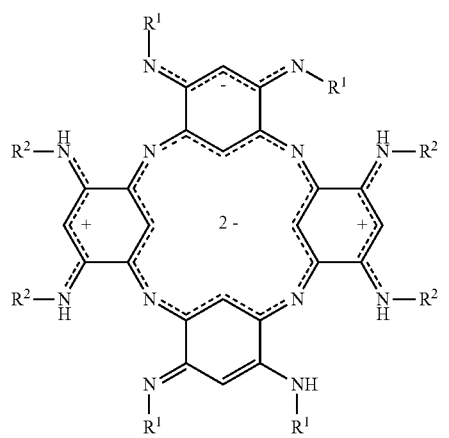
(Ic)

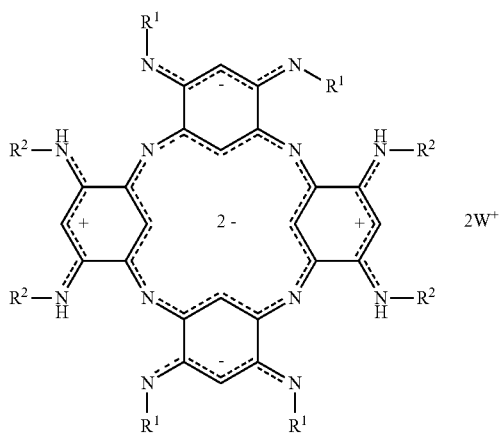
(Id)

or

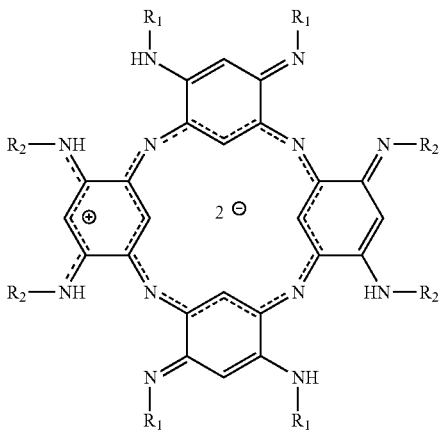
(Ic')

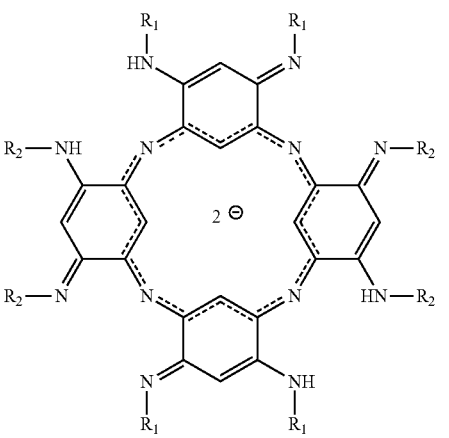
(Id')

wherein W represents Na, $NHEt_3$, Li.

Preferably, the compounds in ionic form are of formula (Ic') and (Id').

As mentioned above, the invention also relates to compounds of formula (I) in the form of chelates since Density Functional Theory (DFT) calculation (as shown in the examples) revealed the possible stabilization of high oxidation state metals in the center (metal having a degree of oxidation of 4 which could link covalently with four carbon atoms of the central ring) and/or the metallation of the external parts (metal having a degree of oxidation of 2 which could be linked to the nitrogens at the periphery of the macrocycle. In a particular embodiment, the metal is for example tetracoordinated, pentacoordinated or hexacoordinated. Those compounds in their chelate form can be as following (Ie)-(Ii):

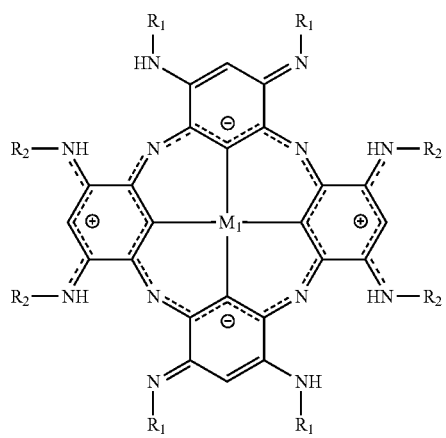

(Ie)

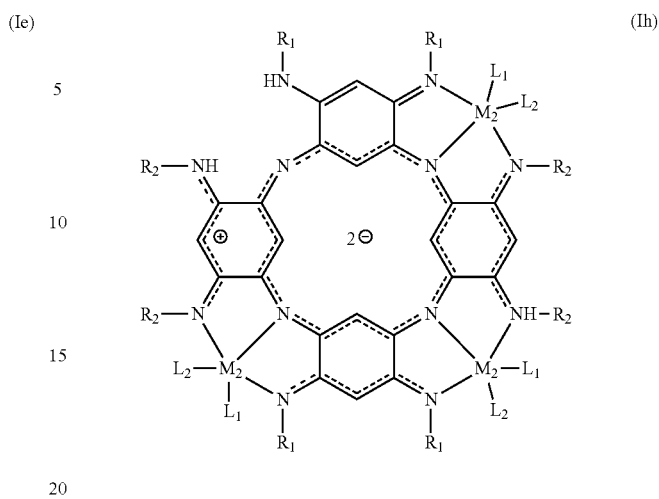

(Ih)

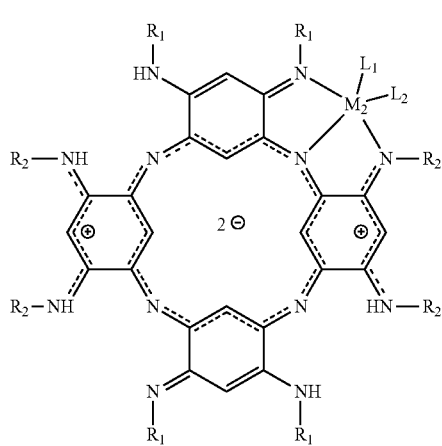

(If)

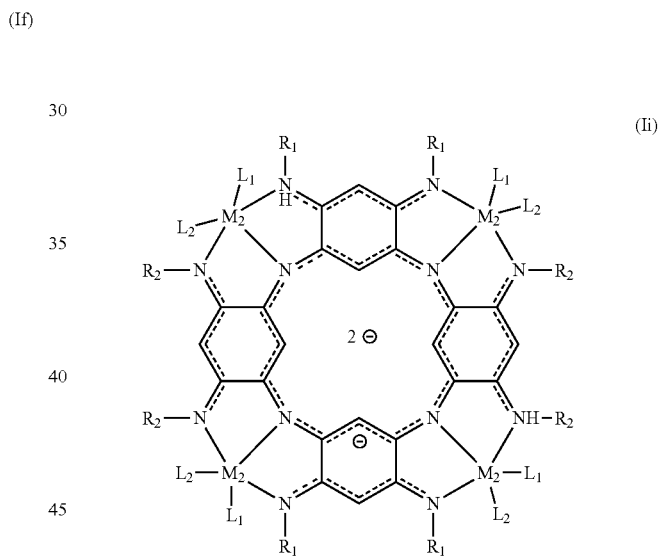

(Ii)

(Ig)

wherein $R_1$ and $R_2$ are defined as above, $M_1$ is chosen among the transition metals having a degree of oxidation of 4 and $M_2$ is chosen among the transition metals having a degree of oxidation of 2 or lanthanides. $M_1$ is preferably chosen among vanadium, titanium, iridium and platinum. $M_2$ is preferably chosen among palladium, nickel, cobalt, zinc, iron, europium, cerium, gadolinium, lanthane.

$L_1$ and $L_2$, identical or different, is a monodentate, bidentate or tridentate ligand, preferably is a ligand which can give 1 covalent bond or 2 electrons, and/or may be optionally bound together. $L_1$ and $L_2$ can form together a group acac (L is O and the L and the two L are bound together), an amine, a phosphine, an aryl, or a halogen. In a particular embodiment in order to have tetracoordinate, pentacoordinate or hexacoordinate that the complex comprises m L, L being chosen among 2 to 6.

In an embodiment, the compounds in their chelate form can be as following (Ij)-(In):

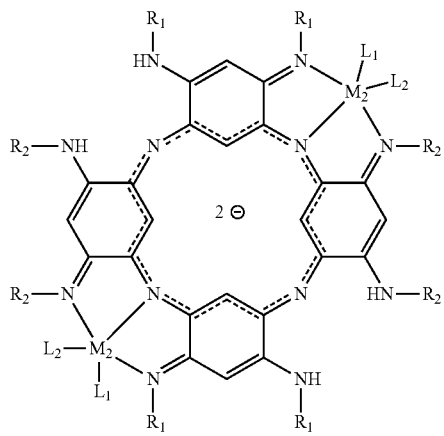
(Ij)

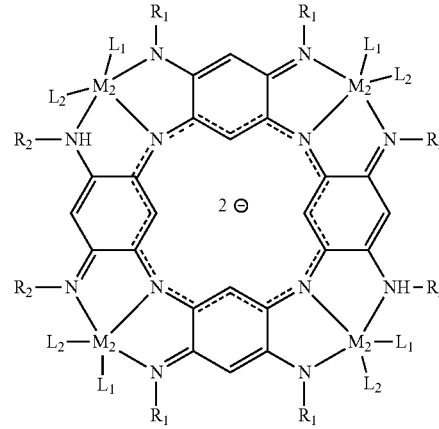
(Im)

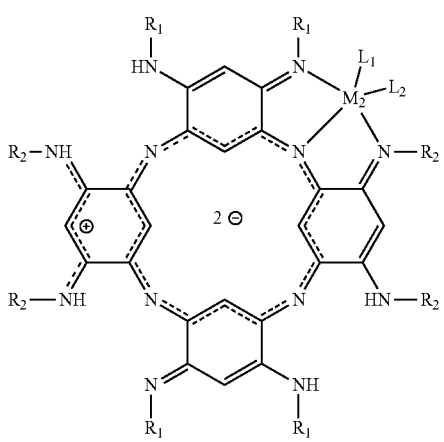
(Ik)

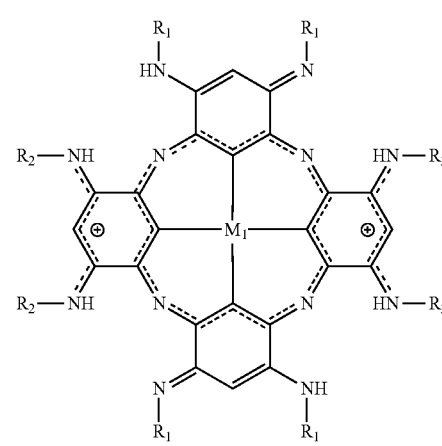
(In)

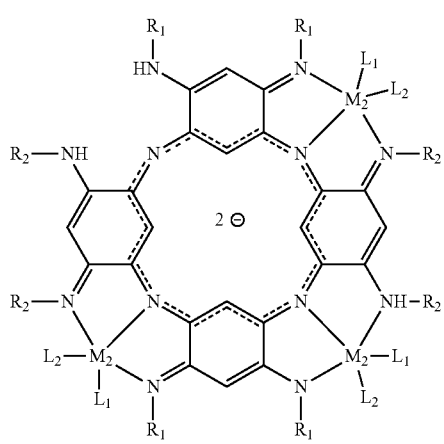
(Il)

wherein $R^1$ and $R^2$ are defined as above, $M_1$ is chosen among the transition metals having a degree of oxidation of 4 and $M_2$ is chosen among the transition metals having a degree of oxidation of 2 or lanthanides. $M_1$ is preferably chosen among vanadium, titanium, iridium and platinum. $M_2$ is preferably chosen among palladium, nickel, cobalt, zinc, iron, europium, cerium, gadolinium, lanthane.

$L_1$ and $L_2$, identical or different, is a monodentate, bidentate or tridentate ligand, preferably is a ligand which can give 1 covalent bond or 2 electrons, and/or may be optionally bound together. $L_1$ and $L_2$ can form together a group acac (L is O and the L and the two L are bound together), an amine, a phosphine, an aryl, or a halogen. It is also possible, in order to have tetracoordinate, pentacoordinate or hexacoordinate that the complex comprises m L, L being chosen among 2 to 6.

The chelation of those metals can enable to improve the Eg gap of the molecules and also to absorb in infrared.

According to the present invention, the terms below have the following meanings:

an aromatic compound contains a set of covalently bound atoms with specific characteristics:
1. A delocalized conjugated π system, most commonly an arrangement of alternating single and double bonds
2. A structure with all the contributing atoms of the aromatic ring in the same plane
3. Contributing atoms arranged in one or more rings 4. A number of π delocalized electrons that is 4n'+2, where n' is an integer from 0 to 4. In the present invention n' is 4;
- a halogen atom corresponds to a fluorine, chlorine, bromine or iodine atom;
- an alkyl group corresponds to a saturated, linear or branched aliphatic group having from 1 to 30 carbon atoms, preferably from 1 to 18 carbon atoms, for example from 1 to 10 carbon atoms.
- a cycloalkyl group corresponds to a cyclic alkyl group comprising from 3 to 6 members. The following examples may be cited: cyclopropyl, cyclobutyl, cyclopentyl, cyclohexyl, etc;
- a heterocycle group is preferably a 5 to 10-membered cycle comprising at least one heteroatom, for example 1, 2 or 3 heteroatoms, preferably chosen among N, S or O;
- an heteroaryl group corresponds to an aromatic heterocycle comprising from 5 to 10 members, preferably 5 or 6 members, preferably including from 1 to 3 heteroatoms preferably chosen among N, S or O;
- an aryl group corresponds to an aromatic cycloalkyl comprising from 6 to 10 members, preferably 6 members;
- a transition metal is an element from group 3 to group 12 and period 4 to period 7, except Lr and Lu, of the periodic table of the element;
- a lanthanide is an element of the periodic table having an atomic number from 57 through 71.

It is understood that $(R_i)_j$ is such that for each of the j occurrence $R_i$ must be identical or different.

The compounds according to the present invention are surprisingly stable and could be exposed to air for months as a solid or for days in solution in DMSO without detectable changes. Without being bound to any theory, this high stability is not only due to aromatic behavior of the central ring but most likely to the zwitterionic character of the whole molecule.

Advantageously, the compounds of the invention absorb in all the visible, in UV and in the NIR region, especially between 300 and 1000 nm. Especially, the inventors have shown that the compounds of the invention absorb radiations around 880 nm which is in the NIR region. This specific range of absorbance especially enables to use those compounds in the field of electronics, photovoltaics, optoelectronics and photodynamic therapies.

As mentioned above, the range of absorption can advantageously be modified by modifying the group $R^1$ and $R^2$ and/or by chelating metals.

Advantageously, the compounds of the invention present a Eg gap comprised between 0.5 and 4 eV, preferably between 1 and 4 eV. For example, compound of formula (I) wherein $R^1$ and $R^2$ represent H present a Eg gap of 1.4 eV. This gap is determined by DFT calculations and by experiments (UV absorption) which is a technique well known by the skilled person. The Eg gap obtained for this compound by electrochemical experimentation is of 1.01 eV.

Without being bound to any theory, the inventors have found that the weak HOMO-LUMO gap can be explained on one hand by the dianionic character of the central cycle and on the other hand by the similarity of the frontier molecular orbitals (HOMO and LUMO) which are totally delocalized. The value of this gap is important to determine the possible applications for the molecules. For example in order to be used in optoelectronics or photodynamic therapies, the gap has to be as low as possible.

The value of the gap should be modified by the modification of the group $R^1$ and/or $R^2$ making the compounds of formula (I) highly versatile. The value of the gap should also be modified by chelating compound of formula (I) with metal(s) as mentioned previously.

The compounds of the invention present some electronic properties similar to the compounds disclosed by Qian et al (Chem. Asian. J., 2010, 5, 1006).

As a consequence, in view of their specific structural and electronic properties (especially due to their NIR absorbing properties) as well as their specific versatility, the compounds according to the invention can be used in many fields. For examples, the compounds of the invention could be used in electronics, more specifically in optoelectronics; in the field of photovoltaics; in the field of photonics; in the field of biology, especially in the field of photodynamic therapies.

Especially, when used in photovoltaics, the compounds of the invention having low dimensions and a weak Eg gap have different advantages compared to the polymers actually used: they are easy to synthesize, to functionalize (they are versatile), to purify . . . . Since they absorb in all visible and NIR, the compounds of the invention can be used alone in the photovoltaic cells and there is no need of different molecules as mentioned above. The compounds of the invention can thus be used as components of solar cells, including organic molecular cells, polymer cells and dye-sensitized solar cells. In those cells the compounds of the inventions serve as charge-transport agents and/or absorbing agents.

As mentioned above, the compounds of the invention contain few atoms and absorb in the NIR region which make them good candidates for being used in photodynamic therapies for the treatment of cancer, including those in deep tissues. In photodynamic therapies, the compounds of the invention are used as photosensitizers. The compounds of the invention are very useful in such an application since they can be modified, by modifying the $R^1$ and $R^2$ group or by chelation, which enables to control the absorption range of the light as well as the solubility of the compounds.

The compounds of the invention could also be used as ligand in coordination chemistry since as mentioned above they can make chelate with metals.

The present invention also relates to the use of the compound of formula (I) in solar cells, particularly in organic solar cells and as dye in dye-sensitized solar cell such as Grätzel cell. Indeed, due to their specific properties as mentioned above and especially the Eg gap and the properties of absorption of near IR, the compounds according to the invention are particularly useful as dye for dye-sensitized solar cell. Compounds of the invention where A is an aryl or heteroaryl, monocyclic or polycyclic, are particularly advantageous for the use in dye-sensitized cells especially due to the possible delocalisation of the charge after excitation of the compound by solar radiation.

According to the present invention dye-sensitized solar cell (Grätzel cell), intend to means solar cells comprising two glass plaque defining an inner medium and one of them comprising a porous film of a semi-conductor, for example $TiO_2$, coated with a monolayer of a dye.

The present invention also relates to solar cell, the solar cell can be such as organic solar cells or dye-sensitized solar call such as Grätzel cell, comprising a compound according to the invention. Preferably, the present invention relates to such as dye-sensitized solar cells, comprising two substrates defining an inner medium which comprises a semi-conductor, for example $TiO_2$, and a compound of the invention as a dye.

The invention also concerns a process (P) for the preparation of compounds of formula (I) which comprises the following steps:

i) reacting 1,5-$Q_2$-2,4-dinitrobenzene with tetraminobenzene in the presence of a base, Q, identical or different, being a leaving group;

ii) optionally, when $R^1$ is different from H, reacting the compound obtained in i) with an electrophilic compound comprising the $R^1$ group in the presence of a base;

iii) reduction of the compound obtained in i) or in ii) in the presence of a reducing agent and preferably of an acid;

iv) optionally, when $R^2$ is different from H, reacting the compound obtained in iv) with electrophilic compound comprising the $R^2$ group in the presence of a base;

v) neutralization of compound obtained in iii) or iv) with a base to give compound of formula (I).

The present invention also relates to a process (P1) for the preparation of compound of formula (I) when at least one of $R^1$ or one of $R^2$ is different form H comprising the following steps:

a1) reacting a 1,5-$Q_2$-2,4-dinitrobenzene with 0.5 equivalent of tetraaminobenzene in the presence of a base, Q, identical or different being a leaving group;

b1) reacting the compound obtained in step a1) with one equivalent of a compound derived from tetraaminobenzene in which at least one and at most two of $NH_2$ group is substituted with a group $R^1$ or $R^2$ different from H, in the presence of a base;

c1) reduction of the compound obtained in step b1) in the presence of a reducing agent which under air is converted into compound of formula (I).

The present invention also relates to a process (P2) for the preparation of compound of formula (I) when at least one of $R^1$ or one of $R^2$ is different form H comprising the following steps:

a2) reacting a 1,5-$Q_2$-2,4-dinitrobenzene with 1 equivalent of a compound derived from tetraaminobenzene in which at least one and at most two of $NH_2$ group is substituted with a group $R^1$ or $R^2$ different from H, in the presence of a base, Q, identical or different being a leaving group;

b2) reduction of the compound obtained in step a2) in the presence of a reducing agent which under air is converted into compound of formula (I).

The present invention also relates to a process (P3) for the preparation of compound of formula (I) when at least one of $R^1$ or one of $R^2$ is different form H comprising the following steps:

a3) reacting a 1,5-$Q_2$-2,4-dinitrobenzene with 0.5 equivalent of a compound derived from tetraaminobenzene in which at least one and at most two of $NH_2$ group is substituted with a first group $R^1$ or $R^2$ different from H, in the presence of a base, Q, identical or different being a leaving group;

b3) reacting the compound obtained in step a3) with one equivalent of a compound derived from tetraaminobenzene in which at least one and at most two of $NH_2$ group is substituted with a second group $R^1$ or $R^2$ different from H and different from the one of step a3), in the presence of a base;

c3) reduction of the compound obtained in step b3) in the presence of a reducing agent which under air is converted into compound of formula (I).

Preferably, the reducing agent in process (P), (P1), (P2) and (P3) is chosen among $SnCl_2$; $H_2$, Pd/C; hydrazine; ammonium formate ($NH_4$, $HCO_2$, Pd/C).

Preferably, the leaving group in process (P), (P1), (P2) and (P3) is chosen among halides, triflates ($OSO_2CF_3$), sulfonate esters such as tosylate or mesylate. Preferably the leaving group is chosen among halides. Preferably 1,5-$Q_2$-2,4-dinitrobenzene is 1,5-difluoro-2,4-dinitrobenzene.

Preferably, the electrophilic compound in process (P) is chosen among $XCH(R^3)R^4$; $TsO-CH(R^3)R^4$, $X—[C(R^5)=(CR^6)]_nR^4$, $TsO—[C(R^5)=(CR^6)]_nR^4$, $XCOR^7$, $XSO_2R^8$.

Preferably, steps i), a1), b1), a2), a3) and c3) are carried out in the presence of a solvent, for example acetonitrile.

Preferably steps i), a1), b1), a2), a3) and c3) are carried out at low temperature, for example between −10 and 10° C., especially at 0° C., then the temperature is raised to room temperature, then, finally the reaction is carried out under reflux.

Preferably, in steps i), a1), b1), a2), a3) and c3) the base is for example diisopropylethylamine (DIPEA).

Preferably in steps ii) and iv) the base is chosen among $K_2CO_3$, $NEt_3$.

Preferably, in steps iii) c1, b2 and c3), the reducing agent is used in large excess.

Preferably, in step iii), c1), b2) et c3) are preferably implemented in the presence of an aci, preferably when the reducing agent is $SnCl_2$, the acid is preferably HX, preferably HCl.

In one embodiment, step iii) is implemented in the presence of an acid which is preferably HX, for example HCl.

Preferably, steps iii) c1), b2) and c3) are carried out at a temperature of around 50-100° C., for example 70° C.

Preferably in step v) the base is chosen among NaOH, $K_2CO_3$, $NaHCO_3$, in particular NaOH.

Compounds of formula (Ia) and (Ib) are obtained by reacting compounds of formula (I) with at least one mole of an acid.

Compounds of formula (Ic) and (Id) are obtained by reacting compounds of formula (I) with at least one mole of a base.

Compounds of formula (Ie) to (Ii) are obtained by mixing compounds of formula (I) in solution in a solvent with the metal in solution in a solvent.

Advantageously, the synthetic accessibility to compounds of the invention is straightforward and highly versatile, as substituents on the peripheric nitrogen atoms are easily introduced and can be easily varied for tuning the properties of the compounds (solubility, geometry, donor/acceptor properties . . . )

The following examples describe the synthesis of some compounds according to the invention. These examples are not intended to be limitative and only illustrate the present invention.

EXAMPLES

Example 1

Figure 1:
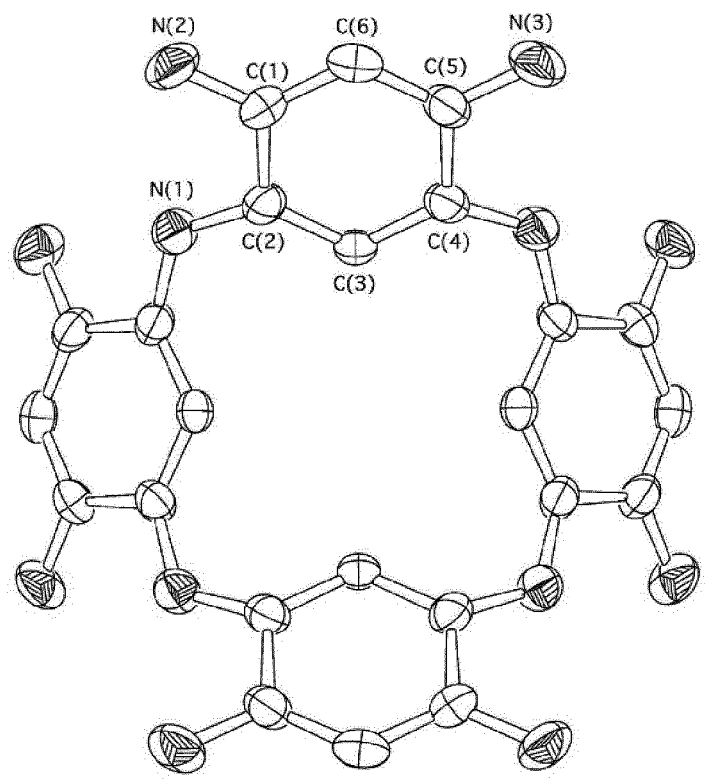
FIG. 1 represents structure of compound (4) (anisotropic displacement parameters at 50%).

Preparation of a Compound 1 of Formula (I) where $R^1$ and $R^2$ Represent H

Step i) Synthesis of Intermediate (2)

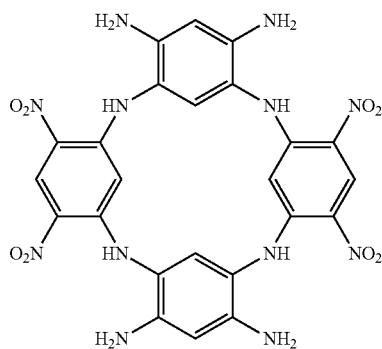

(2)

The commercially available 1,5-difluoro-2,4-dinitrobenzene was reacted with tetranitrobenzene in acetonitrile and in the presence of base (DIPEA) under inert atmosphere at 0° C. The solution was stirred at 0° C. for 2 h, at room temperature for 14 h, and finally under reflux for 5 h. The resulting solid was isolated by filtration and washed with EtOH absolute (abs.) and acetonitrile affording (2) in yield 94%.

$^1$H NMR ((CD$_3$)$_2$SO): δ (ppm)=9.00 (s, 2H), 8.88 (br s, 4H), 6.53 (s, 2H), 6.07 (s, 2H), 5.70 (s, 2H), 4.98 (br s, 8H). $^{13}$C NMR ((CD$_3$)$_2$SO): δ (ppm)=149.3, 145.3, 128.4, 127.8, 124.6, 110.7, 100.1, 93.5.

Elemental Analysis calculated for C$_{24}$H$_{20}$N$_{12}$O$_8$.2H$_2$O: C, 45.00; H, 3.78; N, 26.24. Found: C, 45.56; H, 3.31; N, 25.71.

MS (ESI) m/z=605.1 [M+H]$^+$.

Step iii) Synthesis of Intermediate (3)

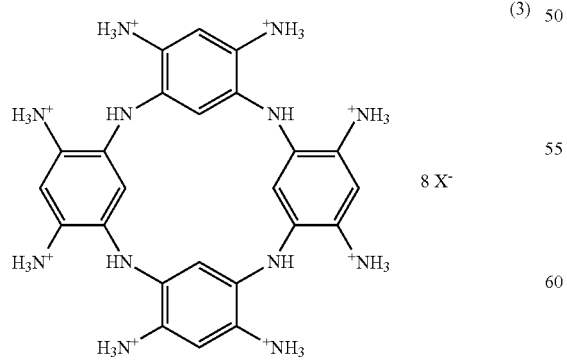

(3)

50 mg of compound (2) and SnCl$_2$ (500 mg, 32 eq) were mixed in a screw-cap vial with 10 mL of HCl. The vial was then sealed with a Teflon-lined cap and placed in an oil bath at 70° C. under stirring for 20 h. The clear yellow suspension was then cooled down to room temperature. 40 mL of HCl was mixed in the suspension and placed in an ultrasound bath for 10 min. The resulting solid (3) (X=Cl) is collected by filtration and washed with MeCN/HCl and Et$_2$O in yield 65%

$^1$H NMR ((CD$_3$)$_2$SO): δ (ppm)=9.27 (bs, 4H), 8.77 (s, 2H), 7.35 (m, 8H), 4.98 (s, 2H). $^{13}$C solid NMR: δ (ppm)=147.3, 135.9, 131.8, 130.2, 126.7, 125.1, 123.7, 98.7.

v) Compound of Formula (1) ($R^1$=$R^2$=H)

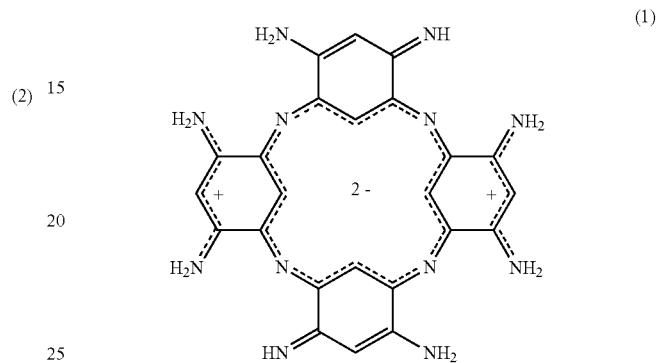

(1)

20 mg of (3) was dissolved in 50 ml of water and the solution was placed in an ultrasound bath preheating at 40° C. NaOH aq. (10%) was then added dropwise to the solution. The neutralization was finished at pH=12 and the mixture was kept in the bath for additional 30 min. The resulting solid was collected by filtration and washing with hot water affording (1) as a dark green solid in yield 84%.

$^1$H NMR ((CD$_3$)$_2$SO): δ (ppm)=8.92 (br s, 7H), 8.61 (br s, 7H), 6.34 (s, 4H), −2.05 (s, 4H).

MS (ESI): 479.21 ([M+H]$^+$).

In order to quantify the aromaticity of compound (1), the nucleus-independent chemical shifts, NCIS(0) and NCIS(1) were calculated at the center of the ring (Chen et al., Chem. Rev., 2005, 105, 3842). The result (−6 ppm for both) shows a strongly diatropic value in agreement with an aromatic compound.

Example 2

Preparation of a Compound 4 of Formula (Ib) where $R^1$ and $R^2$ Represent H and Z is Cl

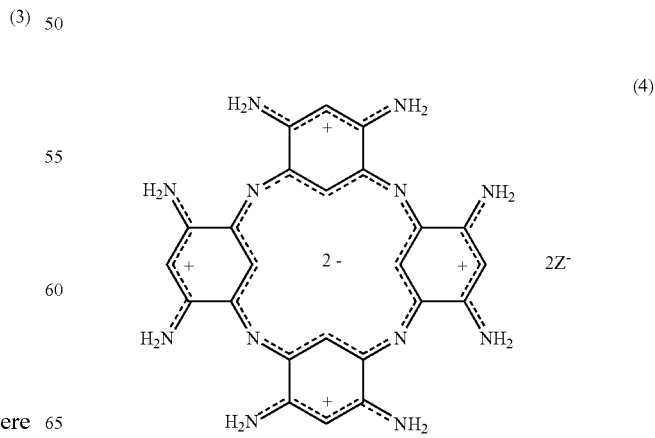

(4)

Protonation of (1) with HCl furnished the protonated species (4) that could be fully characterized by X-ray analysis.

An x-ray diffraction study on single crystals of compound (4) confirmed the features deduced from the spectroscopic data. The eight atoms constituting the diamine-benzoquinonediimine moiety do perfectly fit within a plane (the maximum deviation from planarity is equal to 0.034(7) A). The dihedrals around the nitrogens connecting the cycles are close to 160° and the angle between planes of opposite diamine-benzoquinonediimine is 75°. Hence macrocycle (1) adopts a nonplanar saddle conformation due to the repulsion of the internal C—H hydrogens. Consistently, theoretical calculations on compound (4) confirmed that the D2d structure is a true minima of the potential energy surface.

The bond distances were analyzed in compound (4) according to FIG. 1. In FIG. 1, hydrogen atoms and solvent molecules are omitted for clarity.

The analysis gives the following bond length (Å): N(1)-C(2)=1.337, C(2)-C(3)=1.374, C(3)-C(4)=1.374, C(4)-C(5)=1.455, C(2)-C(1)=1.459, N(2)-C(1)=1.311, C(1)-C(6)=1.362, C(6)-C(5)=1.365, C(5)-N(3)=1.314.

Examination of the bond distances within the N(1)-C(2)-C(3)-C(4) and N(2)-C(1)-C(6)-C(5)-N(3) moieties in compound (4) reveals a bond equalization due to the delocalization of the negative and positive charges, respectively (FIG. 1). The C(1)-C(2) and C(4)-C(5) distances of 1.459 and 1.455 Å, respectively, that would indicate the lack of delocalization between the aromatic cycle and the external π-subunits of the molecule, as already observed in porphyrins 1 (R=Ph) (Gros et al., J. Porphyrins Phtalocyanines, 1997, 1, 201). As a result, compound (4) is a diprotonated zwitterion that can be formally regarded as a combination of: i) an aromatic ring in which the two negative charges are stabilized by intramolecular delocalization, and ii) four cyanine-type subunits which are mutually connected by two C—C single-type bonds to the ring.

The intensity data were collected at 193 K on a Bruker-Nonius KappaCCD diffractometer using MoKα radiation (λ=0.71073 Å). Data collection was performed with COLLECT (Nonius, 2001), cell refinement and data reduction with DENZO/SCALEPACK (Otwinowski & Minor, 1997). The structure was solved with SIR92 (Altomare et al., 1994) and SHELXL-97 (Sheldrick, 2008) was used for full matrix least squares refinement. Compound (4) crystallizes with disordered DMSO and water solvent molecules as well as with chloride anions. The molecule is centered on a four-fold axis and the asymmetric unit is composed of one diamino-benzoquinoneimine unit, one disordered molecule of DMSO in general position split on two sites with occupations of 0.8 and 0.2, one partial DMSO in special position (multiplicity 2, occupation 0.25) sharing the same site than a partial water molecule in general position (occupation 0.25) and 2.5 disordered and partial water molecules lying on a four-fold axis and split on 4 sites (multiplicities 4, occupations 0.05, 0.25, 0.2 and 0125 respectively). A chloride anion lying on a mirror (multiplicity 2, occupation 0.5) is completing the asymmetric unit.

The hydrogen atoms on the amines were located experimentally on the Fourier difference map but they were repositioned as well as the other H-atoms on the carbons and refined as rigid groups. The Uiso parameters for the aromatic and amine hydrogens were fixed to 1.2 Ueq (parent atom) and those for the methyl fixed to 1.5 Ueq (parent atom).

Hence, these two $NH_2$ are engaged into H-bond interactions with the chlorine atoms and the oxygen of co-crystallized DMSO molecules. the N1---Cl1, N1---O1$^i$, N2---Cl1$^{ii}$ and N2---O1$^{iii}$ distances are equal to 3.167 (7) Å, 2.917 (14) Å, 3.161 (7) Å and 2.910 (13) Å respectively and the corresponding D-H---A angles are equal to 178°, 146°, 180° and 146° respectively (symmetry codes: i=0.5-x, 0.5-y, 0.5-z; ii=y, -x, z; iii=0.5-y, -0.5+x, 0.5-z).

Example 3

Preparation of a Compound (5) of Formula (I) where Two of $R^1$ Represent H Two of $R^1$ Represent CH COOH and $R^2$ Represents H Step a1) Synthesis of Intermediate (a1)

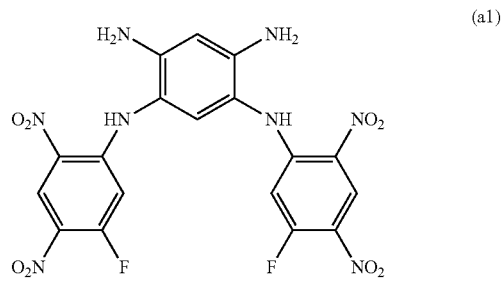 [SMILES: Nc1cc(N)c(Nc2cc(F)c([N+](=O)[O-])cc2[N+](=O)[O-])cc1Nc1cc(F)c([N+](=O)[O-])cc1[N+](=O)[O-]]

The commercially available 1,5-difluoro-2,4-dinitrobenzene was reacted with 0.5 equiv. of tetraaminobenzene in the presence of base (DIPEA) under inert atmosphere. The solution was stirred at 0° C. for 14 h and the resulting solid was isolated by filtration and washed affording (a1).

Step b1 Synthesis of Intermediate b1 with R1=$CH_2COOH$

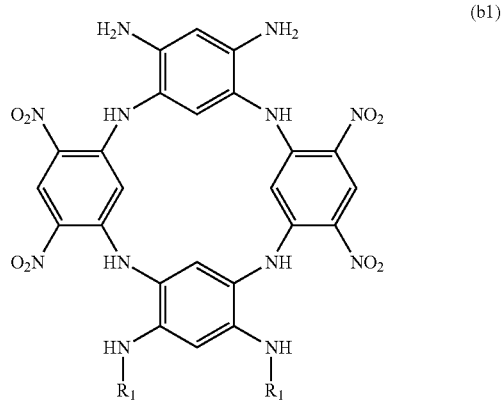

The triaryl derivative (a1)) was reacted with 1 equiv. of disubstituted tetraaminobenzene bearing two $CH_2COOH$ groups—that could be prepared in two steps from 1,5-difluoro-2,4-dinitrobenzene and primary amines bearing COOH functions—in the presence of base (DIPEA) under inert atmosphere. The solution was stirred and the obtained solid was isolated by filtration and washed affording (b1).

Step b3 Synthesis of (5) with R1=CH$_2$COOH

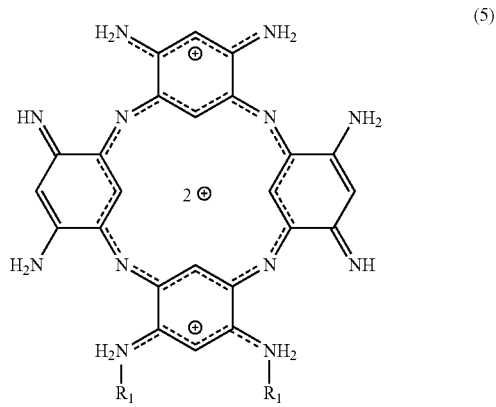

Tetranitro-azacalixphyrins (b1) were then reacted in the presence of reducing agent under inert atmosphere affording the corresponding octaamino-azacalixphyrins—not isolated—which under air are converted into azacalixphyrins (5).

Example 4

Preparation of a Compound (6) of Formula (I) where Four of $R^1$ Represent H and $R^2$ Represents H Step a2) Synthesis of Intermediate a2 with R1=CH$_2$COOH

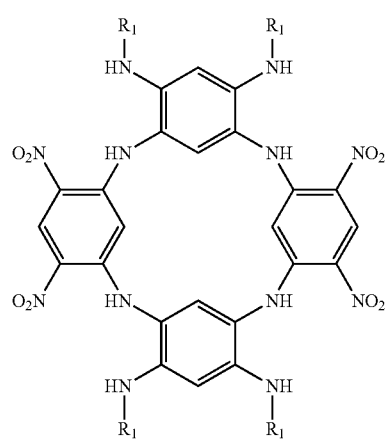

The commercially available 1,5-difluoro-2,4-dinitrobenzene was reacted with 1 equiv. of disubstituted tetraaminobenzene comprising two CH$_2$COOH groups—that could be prepared in two steps from 1,5-difluoro-2,4-dinitrobenzene and primary amines bearing COOH functions—in the presence of base (DIPEA) under inert atmosphere. The solution was stirred and the obtained solid was isolated by filtration and washed affording (a2).

Steps b2) Synthesis of Target (6) with R1=CH$_2$COOH

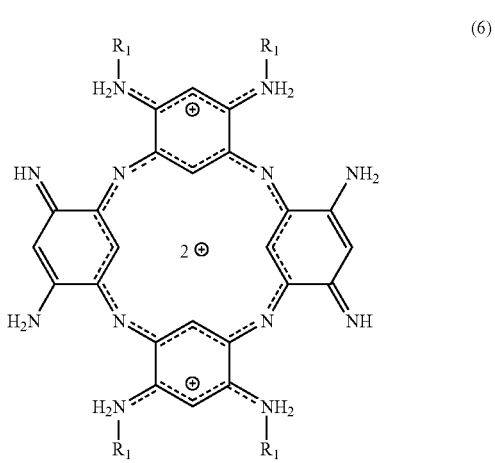

Tetranitro-azacalixphyrins (a2) were then reacted in the presence of reducing agent under inert atmosphere affording the corresponding octaamino-azacalixphyrins—not isolated—which under air are converted into azacalixphyrins (6).

Example 5

Preparation of a Compound (7) of Formula (I) where Two of $R^1$ Represent H and Two of R1 Represent a n-Butyl Group Step a3) Synthesis of Intermediate (a3)

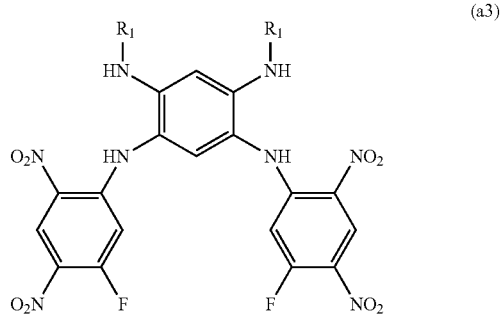

The commercially available 1,5-difluoro-2,4-dinitrobenzene was reacted with 0.5 equiv. of disubstituted tetraaminobenzene carrying two group R1=CH$_2$COOH—that could be prepared in two steps from 1,5-difluoro-2,4-dinitrobenzene and primary amines bearing COOH functions—in the presence of base (DIPEA) under inert atmosphere. The solution was stirred and the crude product was purified by column chromatography (SiO$_2$) affording (a3).

Step b3) Synthesis of Intermediate (b3)

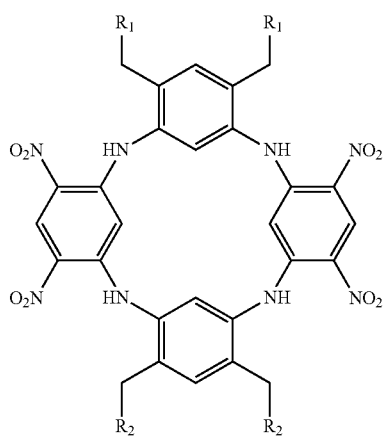

The triaryl derivatives (a3) were reacted with 1 equiv. of dialkyltetraaminobenzene bearing two R2=nbutyl groups—that could be prepared in two steps from 1,5-difluoro-2,4-dinitrobenzene and primary alkylamines—in the presence of base (DIPEA) under inert atmosphere. The solution was stirred and the crude product was purified by column chromatography (SiO$_2$) affording (b3).

Step c3) Synthesis of Target (7)

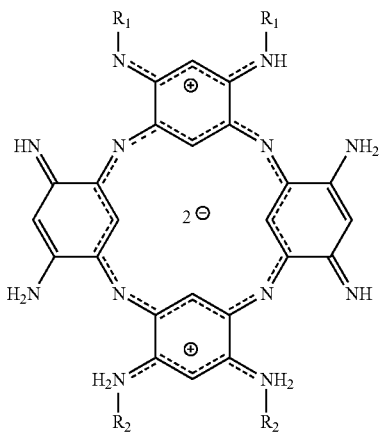

Tetranitro-azacalixphyrins (b3) were then reacted in the presence of reducing agent under inert atmosphere affording the corresponding octaamino-azacalixphyrins—not isolated—which under air are converted into azacalixphyrins (7).

Example 6

Theoretical Calculations

Methods

All simulations have been achieved with Gaussian09 program, applying default procedures, integration grids, algorithms and parameters, except for tighten SCF ($10^{-9}$ a.u.) and internal forces ($10^{-5}$ a.u.) convergence thresholds. We have adopted a multi-step strategy that is efficient to determine the UV/Vis features of most organic dyes. It proceeds as: 1) the (gas phase) ground-state geometrical parameters have been determined at the PBE0/6-311G(2d,2p) level via a force-minimization process; 2) the vibrational spectrum of each derivatives has been determined analytically at the same level of theory, that is PBE0/6-311G(2d,2p), and it has been checked that all structures correspond to true minima of the potential energy surface; 3) structures have been reoptimized at the same level of theory including the PCM model so to account for environmental effects, 4) the first ten low-lying excited-states have been determined within the vertical TD-DFT approximation using the PBE0/6-311++G(2d,2p) level of approximation; 5) the NMR shieldings of the protons have been computed with he the well-known GIAO scheme with the PBE0 functional and the cc-pVTZ basis set, using TMS computed in the same conditions as reference values; 6) NICS have been computed following the methodology proposed by Schleyer and coworkers, that is rely on the B3LYP/6-311+G (d,p) approach for both structures and NMR shifts. The orbitals represented in this manuscript use a 0.03 a.u. contour threshold.

Metal-Containing Structures

Figure 2:
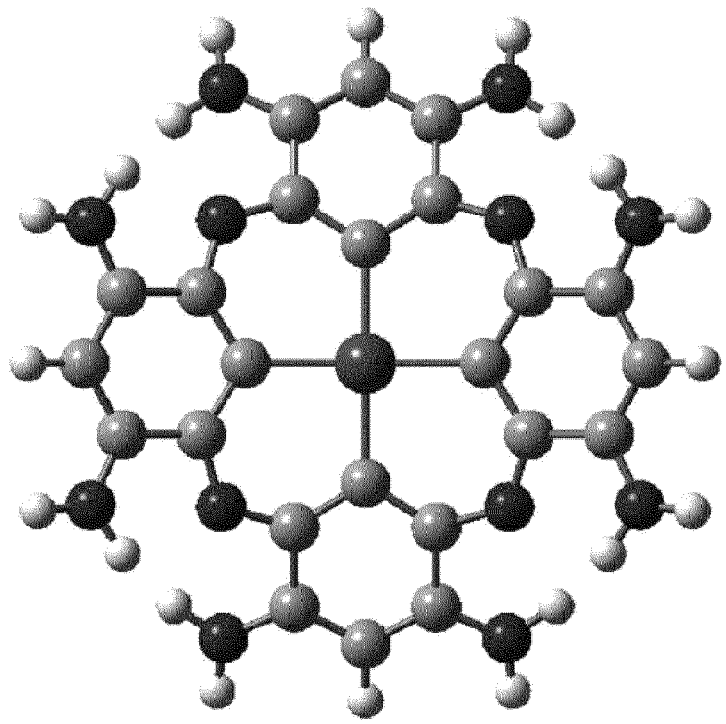
FIG. 2 represents the DFT optimized structures for Pt-4.
Figure 3:
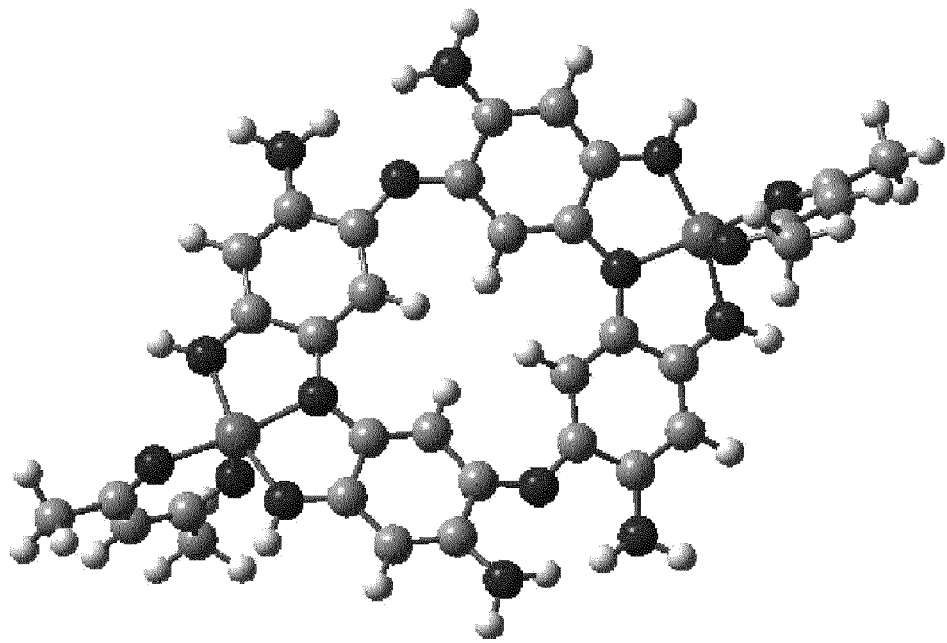
FIG. 3 represents the DFT optimized structures for a dicobalt complex.

The same theoretical methodology was used to evaluate complexes structures based on the compound (4). First, we have replaced the central protons by a single platinum ion ($Pt^{4+}$) and have been able to locate a true minima of the potential energy surface (no imaginary frequency at the PBE0/6-311G(2d,2p) level, using LanL2DZ pseudopotentials for the heavy ion and selecting a $D_{2d}$ point group) for a compound with the central ion in a nearly square planar environment (FIG. 2). In addition, DFT calculations also demonstrate that complexation might occur on the side of the system, as illustrated by the di-cobalt structure displayed in FIG. 3 (true minima at the same level of theory as for Pt structure).

Example 7

Figure 4:
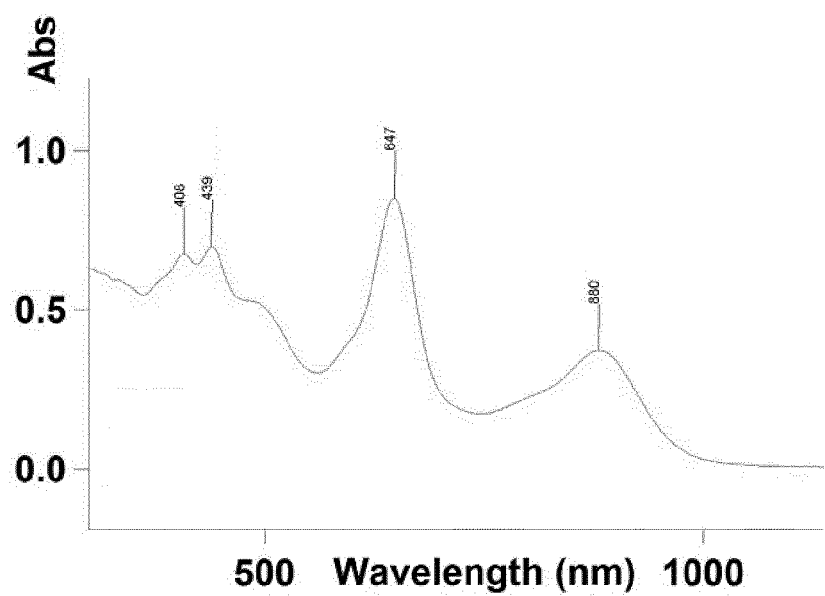
FIG. 4 represents UV-visible-NIR absorption spectrum of compound (4) in DMSO.
Figure 5:
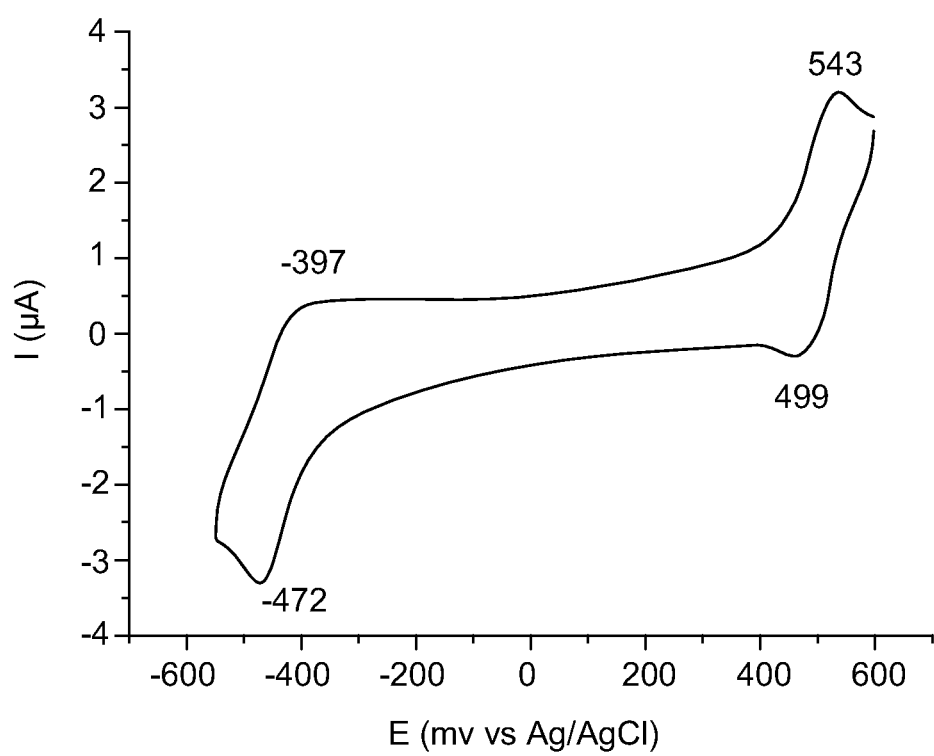
FIG. 5 represents a cyclic voltammogram obtained for compound (1) of example 1.

UV-Vis-NIR Absorption Spectrum of Compound (4) or (1) in DMSO and Calculation of the Clap Eq The absorption spectrum of compound (4) (the similar spectrum is obtained for compound (1)) (FIG. 4) exhibits in DMSO three main bands in the visible at A=408, 439 (with shoulder) and 647, and an additional broad absorption in the NIR region (ca. 880 nm). PCM-TD-PBE0/6-311++G(2d,2p) calculations on compound (4) were performed to gain insights into the nature of the two first bands. The first absorption is predicted at 887 nm and is significantly dipole-allowed (oscillator strength, f, of 0.2).

This value is in remarkable agreement with the measurements at 880 nm. It is clearly a highly-delocalized excited-state, with a partial charge-transfer occurring through the 6-like bond (a finding typical of alternating systems)—from the imine to the amine subregions. This enhanced delocalization accounts for its relatively small transition energy. The next significant band is computed at 588 nm (f=0.4) and it corresponds to the strong 647 nm experimental band, the error being in the line of the TD-DFT accuracy. Like the first absorption, this excitation implies a full electronic reorganization, but with no marked CT character. The HOMO-LUMO gap computed at the PBE0/6-311G(2d,2p) level is 1.65 eV (for compound (1)) and 2.31 eV (for compound (4)) which can be compared to 3.28 eV for the zinc porphyrin.

Example 8

Electrochemical Studies

Cyclic voltammetric (CV) data of compound (1) of example 1 were acquired using a BAS 100 Potentiostat (Bio-analytical Systems) and a PC computer containing BAS100W software (v2.3). A three-electrode system with a Pt working electrode (diameter 1.6 mm), a platinum counter electrode and an Ag/AgCl (with 3 M NaCl filling solution) reference electrode was used. The compound was studied at $1 \cdot 10^{-3}$ M in DMSO/TBAClO$_4$ 0.1 M. and cyclic voltammogram recorded at a scan rate of 250 mV·s$^{-1}$. Ferrocene was used as internal standard.

The CV exhibited a reversible redox wave at 0.543V vs Ag/AgCl resulting from a two electrom oxidation process ($\Delta E_{1/2}(ox)=0.521$ V). Such compound could be similarly reduced at 0.472 V ($\Delta E_{1/2}(red)=-0.435$ V), leading to an electrochemical HOMO/LUMO gap of 1.01 eV (Eg) also in the line of the DFT calculations.

Example 9

Preparation and Photovoltaic Measurement of a GräTzel Cell

FTO conductive glass substrates (F-doped SnO$_2$) were cleaned by successive sonication in soapy water, then an ethanolic solution of HCl (0.1 M) for 10 minutes, and finally dried in air. TiO$_2$ films were then prepared in three steps. A first treatment is applied by immersion for 30 min in an aqueous TiCl$_4$ solution at 80° C. Layers of TiO$_2$ were then screen printed with transparent colloidal paste DSL 18NR-T and light scattering DSL 18NR-AO (Dyesol) as final layer, with 20-minute long drying steps at 150° C. between each layer. The obtained substrates were then sintered at 450° C., following a progressive heating ramp (325° C. for 5 min, 375° C. for 5 min, 450° C. for 30 min). A second TiCl$_4$ treatment was immediately conducted afterwards. Thicknesses were measured by a Sloan Dektak 3 profilometer and are in the range of 12 μm. The prepared TiO$_2$ electrodes were soaked while still hot (80° C.) in a 0.1 mM solution of the dye in a suitable solvent for 12 hours. Solar cells were prepared using the dye-sensitized electrodes as the working electrodes and platinum-coated conducting glass electrodes as counter electrodes. The latter were prepared by chemical deposition of platinum from hexachloroplatinic acid in distilled isopropanol (2 mg per mL) and subsequent firing at 380° C. for 20 minutes. The two electrodes were placed on top of each other and sealed using a thin transparent film of Surlyn polymer (DuPont, 25 μm) as a spacer to form the electrolyte space. A drop of electrolyte was introduced by vacuum back filling through a predrilled hole in the counter electrode, and the photovoltaic device was sealed afterwards with surlyn and a cover glass. The cell had an active area of ca. 0.25 cm$^2$. The current-voltage characteristics were determined by applying an external potential bias to the cell and measuring the photocurrent using a Keithley model 2400 digital source meter. The overall conversion efficiency (η) of the photovoltaic cell is calculated from the integral photocurrent density (Jsc), the open-circuit photovoltage (Voc), the fill factor of the cell (FF), and the intensity of the incident light (IPh). The photovoltaic cell was illuminated with an Oriel lamp calibrated to AM 1.5 (air mass) intensity (1000 W·m$^{-2}$).

The invention claimed is:
1. Compound of formula (I)

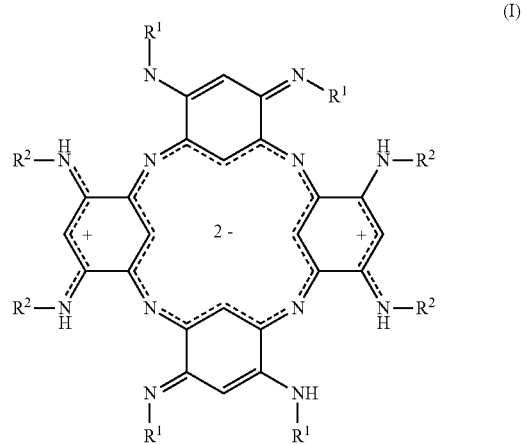

in which:
/// represents a single bond or a double bond provided that the central ring comprising 16 members (4 nitrogen atom and 12 carbon atoms) is an aromatic ring;

each $R^1$ and $R^2$ are identical or different and represent:
a hydrogen atom;
a group of formula —CH($R^3$)$R^4$;
a group of formula —[C($R^5$)=(C$R^6$)]$_n$$R^4$;
a group of formula —C(O)$R^7$; or
a group of formula SO$_2$$R^8$;

$R^3$ represents H, an aliphatic chain, linear or branched, having from 1 to 30 carbon atoms;

$R^4$ represents an aliphatic chain, linear or branched, having from 1 to 10 carbon atoms, H, X, OH, O$R^3$, SH, S$R^3$, CH(O), C(O)OH, CX(O), C(O)O$R^3$, C(O)NH$R^3$, C(O)NH$_2$, NH$R^3$, NRR', an heteroaryl, an aryl, CN, NO$_2$, heterocycle or cycloalkyl, the heteroaryl, aryl, heterocycle or cycloalkyl is optionally substituted by one or more alkyl, linear or branched, having from 1 to 10 members, X, NRR', OR;

$R^5$ and $R^6$, identical or different, represent $R^3$, X, OH, O$R^3$, SH, S$R^3$, CH(O), C(O)OH, CX(O), C(O)O$R^3$, C(O)NH$R^3$, C(O)NH$_2$, NRR', an heteroaryl, an aryl, CN, NO$_2$, heterocycle or cycloalkyl, the heteroaryl, aryl, heterocycle or cycloalkyl is optionally substituted by one or more alkyl, linear or branched, having from 1 to 10 members, X, NRR', OR;

n is an integer from 1 to 10;

$R^7$ represents CH$R^3$$R^4$, heteroaryl or aryl, the heteroaryl or aryl is optionally substituted by one or more alkyl, linear or branched, having from 1 to 10 members, X, NRR', OR;

$R^8$ represents heteroaryl or aryl, the heteroaryl or aryl is optionally substituted by an alkyl, linear or branched, having from 1 to 10 members, X, NRR', OR;

X represents an halogen atom;

R, R', identical or different, represent hydrogen, an aliphatic chain, linear or branched, having from 1 to 30 carbon atoms, or an aryl, the aryl is optionally substituted by one or more alkyl, linear or branched, having from 1 to 10 members, X, OH, NH$_2$;

and the corresponding compound in ionic forms and in their chelated forms with metals.

2. Compound according to claim 1, of formula (Ia), (Ib), (Ic), (Id), (Ic') or (Id'):
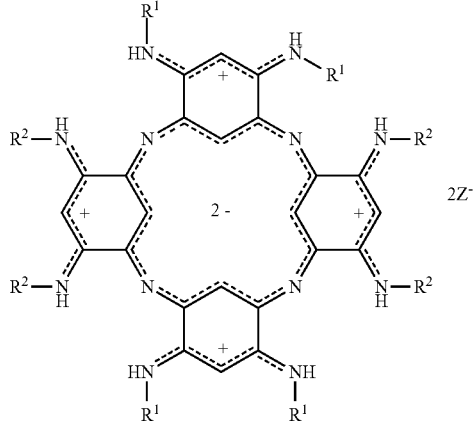
(Ib)
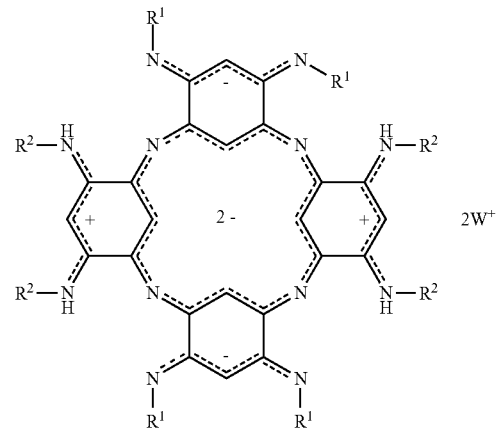
(Id)
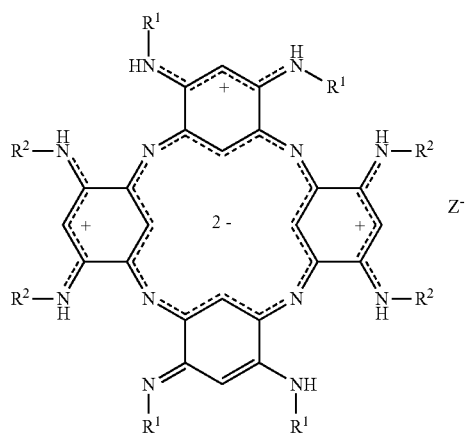
(Ia)
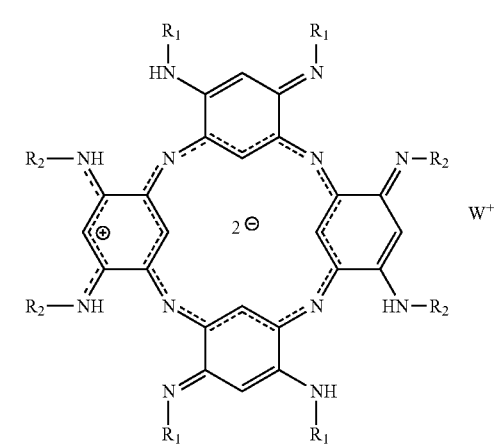
(Ic')
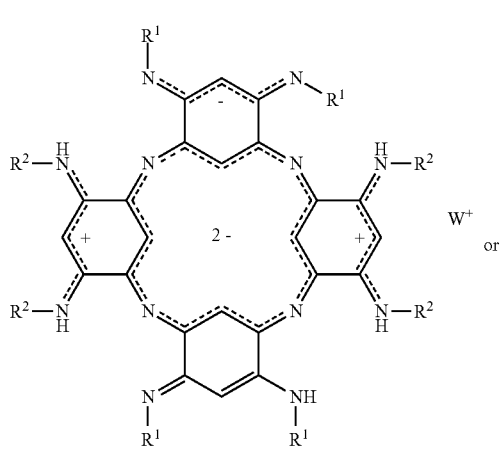
(Ic)
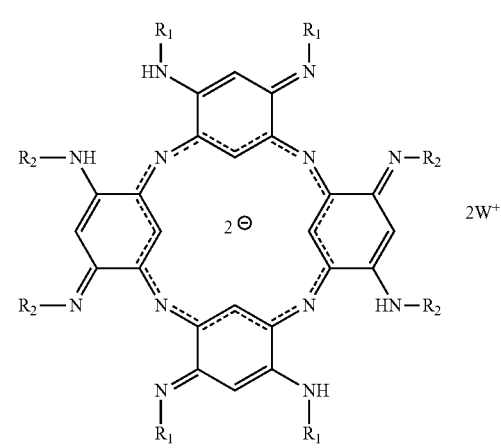
(Id')
wherein $R_1$ and $R_2$ are defined as in claim 1, Z represents X or $CF_3COO$ and W represents Na, Li, $Net_3$.

3. Compound according to claim 1, of formula (Ij)-(In):

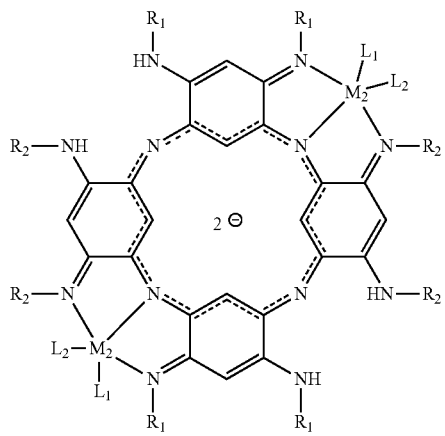
(Ij)

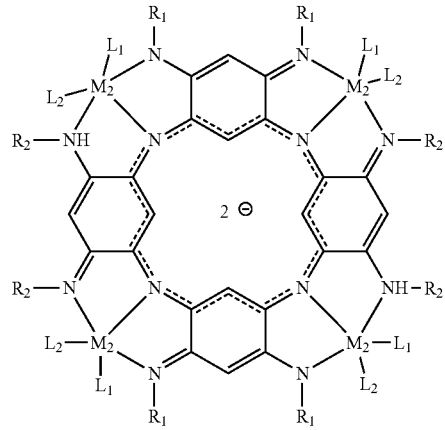
(Im)

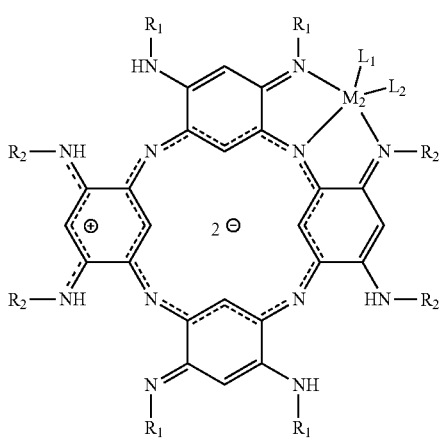
(Ik)

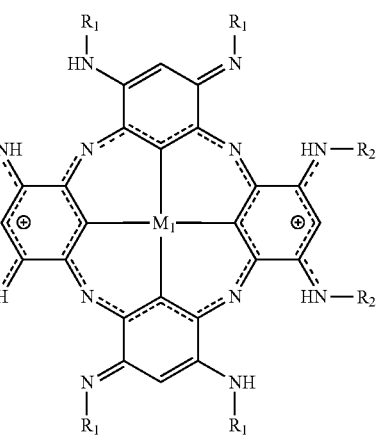
(In)

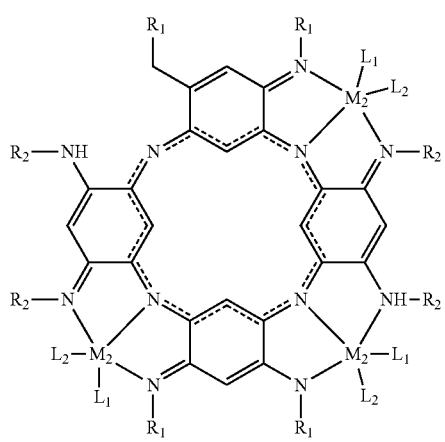
(Il)

wherein $R_1$ and $R_2$ are defined as in claim 1, $M_1$ is chosen among the transition metals having a degree of oxidation of 4 and $M_2$ is chosen among the transition metals having a degree of oxidation of 2 or lanthanides;

$L_1$ and $L_2$, identical or different, is a ligand which can give 1 covalent bond or 2 electrons, and/or may be optionally bound together.

4. Compound according to anyone of claims 1 to 3, wherein $R^3$ represents an alkyl, linear or branched, having from 1 to 18 carbon atoms.

5. Compound according to anyone of claims 1 to 3, wherein $R^1$ and $R^2$ are H.

6. Compound according to anyone of claims 1 to 3, wherein $R^1$ and $R^2$, identical or different are H or —$C(R^3)R^4$ or alkyl, where $R^3$ is H or an aliphatic chain with 1 to 30 carbon atoms and $R^4$ is COOH or an aliphatic chain with 1 to 30 carbon atoms.

7. Compound according to anyone of claims 1 to 6, having a Eg gap comprised between 1 and 4 eV.

8. Compound according to anyone of claims 1 to 7, absorbing in all the visible and in the NIR region.

9. Process for the preparation of compounds according to anyone of claims 1 and 4 to 8, comprising the following steps:

i) reacting 1,5-$Q_2$-2,4-dinitrobenzene with tetraminobenzene in the presence of a base, Q, identical or different, being a leaving group;

ii) optionally, when $R^1$ is different from H, reacting the compound obtained in i) with an electrophilic compound comprising the $R^1$ group in the presence of a base;
iii) reduction of the compound obtained in i) or in ii) in the presence of a reducing agent and eventually of an acid;
iv) optionally, when $R^2$ is different from H, reacting the compound obtained in iv) with electrophilic compound comprising the $R^2$ group in the presence of a base;
v) neutralization of compound obtained in iii) or iv) with a base to give compound of formula (I).

10. Process for the preparation of compounds according to anyone of claims 1 to 4, 6 to 8 comprising the steps of:
   a1) reacting a 1,5-$Q_2$-2,4-dinitrobenzene with 0.5 equivalent of tetraaminobenzene in the presence of a base, Q, identical or different being a leaving group;
   b1) reacting the compound obtained in step a1) with one equivalent of a compound derived from tetraaminobenzene in which at least one and at most two of $NH_2$ group is substituted with a group $R^1$ or $R^2$ different from H, in the presence of a base;
   c1) reduction of the compound obtained in step b1) in the presence of a reducing agent which under air is converted into compound of formula (I).

11. Process for the preparation of compounds according to anyone of claims 1 to 4, 6 to 8 comprising the steps of:
   a2) reacting a 1,5-$Q_2$-2,4-dinitrobenzene with 1 equivalent of a compound derived from tetraaminobenzene in which at least one and at most two of $NH_2$ group is substituted with a group $R^1$ or $R^2$ different from H, in the presence of a base, Q, identical or different being a leaving group;
   b2) reduction of the compound obtained in step a2) in the presence of a reducing agent which under air is converted into compound of formula (I).

12. Process for the preparation of compounds according to anyone of claims 1 to 4, 6 to 8 comprising the steps of:
   a3) reacting a 1,5-$Q_2$-2,4-dinitrobenzene with 0.5 equivalent of a compound derived from tetraaminobenzene in which at least one and at most two of $NH_2$ group is substituted with a first group $R^1$ or $R^2$ different from H, in the presence of a base, Q, identical or different being a leaving group;
   b3) reacting the compound obtained in step a3) with one equivalent of a compound derived from tetraaminobenzene in which at least one and at most two of $NH_2$ group is substituted with a second group $R^1$ or $R^2$ different from H and different from the one of step a3), in the presence of a base;
   c3) reduction of the compound obtained in step b3) in the presence of a reducing agent which under air is converted into compound of formula (I).

13. Process according to claims 9 to 12, wherein the reducing agent is chosen among $SnCl_2$; $H_2$, Pd/C; hydrazine; ammonium formate ($NH_4$, $HCO_2$, Pd/C).

14. Process according to claims 9 to 13, wherein the leaving group is chosen among halides, triflates ($OSO_2CF_3$), sulfonate esters such as tosylate or mesyltate.

15. Process according to claim 9, 13 or 14, wherein the electrophilic compound is chosen among $XCH(R^3)R^4$; TsO-CH($R^3$)$R^4$, X—[C($R^5$)=(C$R^6$)]$_n$$R^4$, TsO—[C($R^5$)=(C$R^6$)]$_n$$R^4$, $XCOR^7$, $TsOCOR^7$, $XSO_2R^8$.

16. Process for the preparation of compound according to claim 2 comprising the reaction of a compound of formula (I) with at least one mole of an acid or with at least one mole of a base.

17. Use of compound of formula (I) according to anyone of claims 1 to 8 in the fields of photovoltaic cells.

18. Use according to claim 17 in solar cells, such as organic solar cells and particularly as dye in dye-sensitized solar cells (Grätzel cells).

19. A complex having as ligand a compound of formula (I) according to anyone of claims 1 to 8.

20. An solar cell, such as organic solar cell and preferably dye-sensitized solar cell (Grätzel cell), comprising a compound according to anyone of claims 1 to 8.

* * * * *